US010978970B2

(12) United States Patent
Umemoto et al.

(10) Patent No.: US 10,978,970 B2
(45) Date of Patent: Apr. 13, 2021

(54) APPARATUS AND CONTROL APPARATUS FOR THE SAME

(71) Applicant: OLYMPUS CORPORATION, Tokyo (JP)

(72) Inventors: Yoshitaka Umemoto, Hachioji (JP); Takashi Suzuki, Hino (JP); Toshihiro Kumagai, Hino (JP); Takuro Onda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/697,639

(22) Filed: Nov. 27, 2019

(65) Prior Publication Data
US 2020/0099320 A1    Mar. 26, 2020

Related U.S. Application Data

(63) Continuation of application No. PCT/JP2018/014936, filed on Apr. 9, 2018.

(30) Foreign Application Priority Data

Jun. 2, 2017    (JP) ............................. JP2017-109931

(51) Int. Cl.
   *H02P 6/06*    (2006.01)
   *A61B 1/00*    (2006.01)
   *H02P 6/24*    (2006.01)

(52) U.S. Cl.
   CPC ............ *H02P 6/06* (2013.01); *A61B 1/00006* (2013.01); *A61B 1/0016* (2013.01); *H02P 6/24* (2013.01)

(58) Field of Classification Search
   CPC ...... H02P 6/06; H02P 6/24; H02P 1/00; H02P 1/04; H02P 4/00; H02P 5/00; H02P 6/00;
   (Continued)

(56) References Cited

U.S. PATENT DOCUMENTS

| 4,631,582 A * | 12/1986 | Nagasaki | ................. | A61B 1/05 |
| | | | | 348/230.1 |
| 4,998,163 A * | 3/1991 | Salvati | .................... | H02P 8/04 |
| | | | | 348/270 |

(Continued)

FOREIGN PATENT DOCUMENTS

| JP | 2014-064686 A | 4/2014 |
| JP | 2014-068817 A | 4/2014 |

(Continued)

OTHER PUBLICATIONS

English translation of International Preliminary Report on Patentability dated Dec. 12, 2019, together with the Written Opinion received in related International Application No. PCT/JP2018/014936.

International Search Report dated Jun. 19, 2018 issued in PCT/JP2018/014936.

*Primary Examiner* — Anthony M Paul
(74) *Attorney, Agent, or Firm* — Scully, Scott, Murphy & Presser, P.C.

(57) ABSTRACT

An apparatus includes a rotation body, a motor, a drive controller, a rotating speed detector, a rotation error determination circuit, and a filter. The rotation body is provided on an outer peripheral surface of an elongated insertion section and configured to be rotatable around a longitudinal axis. The motor rotates the rotation body. The drive controller controls driving of the motor. The rotating speed detector detects a rotating speed of the motor based on an encoder signal output from an encoder. The rotation error determination circuit determines an error in rotation of the rotation body based on the detected rotating speed. The filter passes, as the encoder signal, only a signal having a frequency, outside a frequency band of a high-frequency signal of a high-frequency treatment instrument, of signals input to the rotating speed detector.

14 Claims, 3 Drawing Sheets

(58) Field of Classification Search
CPC .... H02P 6/005; H02P 6/04; H02P 6/08; H02P 6/10; H02P 6/16; H02P 6/17; H02P 7/00; H02P 8/00; H02P 23/00; H02P 27/00; H02P 21/0021; A61B 1/0016; A61B 1/00006; A61B 1/00; A61B 1/00004; A61B 1/00041; A61B 1/00055; A61B 1/00133
USPC .......... 318/400.01, 700, 701, 721, 779, 799, 318/430, 599
See application file for complete search history.

(56) References Cited

U.S. PATENT DOCUMENTS

| | | | | |
|---|---|---|---|---|
| 6,881,188 | B2* | 4/2005 | Furuya | H04N 7/18 348/E7.085 |
| 7,725,013 | B2* | 5/2010 | Sugimoto | G02B 23/2484 396/17 |
| 9,483,037 | B2* | 11/2016 | Shimizu | G05B 19/19 |
| 2014/0094657 | A1* | 4/2014 | Miyamoto | A61B 1/0016 600/114 |

FOREIGN PATENT DOCUMENTS

| | | |
|---|---|---|
| JP | 2016-054841 A | 4/2016 |
| WO | WO 2016/009711 A1 | 1/2016 |
| WO | WO 2016/103966 A1 | 3/2016 |

\* cited by examiner

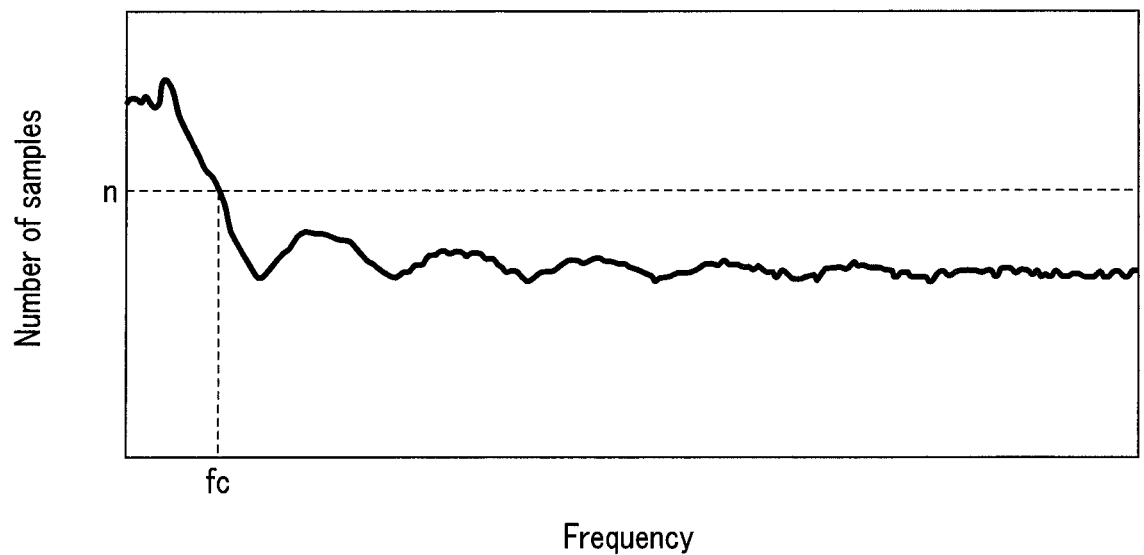
F I G. 2

APPARATUS AND CONTROL APPARATUS FOR THE SAME

CROSS-REFERENCE TO RELATED APPLICATIONS

This application is a Continuation Application of PCT Application No. PCT/JP2018/014936, filed Apr. 9, 2018 and based upon and claiming the benefit of priority from the prior Japanese Patent Application No. 2017-109931, filed Jun. 2, 2017, the entire contents of both of which are incorporated herein by reference.

FIELD

The embodiment relates to an apparatus and a control apparatus for the same.

BACKGROUND

A self-propelled endoscope apparatus is known as an endoscope apparatus to be inserted into a lumen. In the self-propelled endoscope apparatus, for example, an insertion section is moved forward and backward by a propulsive force generated by rotating a rotation body provided around the insertion section by a motor. Such an endoscope apparatus assists an insertion or removal operation of the insertion section by the user.

Here, the motor of the self-propelled endoscope apparatus is feedback-controlled. In this feedback control, the drive of the motor is controlled in accordance with the deviation between the target value corresponding to a foot switch depressed by the user and the measured value of the rotating speed of a motor measured by the encoder provided in the motor. The insertion device proposed in International Publication No. 2016/009711 improves the accuracy of feedback control by removing, by a low-pass filter (LPF), high-frequency noise in an instruction value input from an input unit such as a foot switch.

The self-propelled endoscope apparatus is provided with an error determination unit that determines an error of rotation of the rotation body. This error determination unit determines an error in rotation of the rotation body based on the rotating speed of the motor, when, for example, the rotating speed of the rotation body is more than necessary, or the rotation body is not rotating when necessary.

SUMMARY

According to a first aspect, an apparatus includes a rotation body, a motor, a drive controller, a rotating speed detector, a rotation error determination circuit, and a filter. The rotation body is provided on an outer peripheral surface of an elongated insertion section and configured to be rotatable around a longitudinal axis. The motor rotates the rotation body. The drive controller controls driving of the motor. The rotating speed detector detects a rotating speed of the motor based on an encoder signal output from an encoder. The rotation error determination circuit determines an error in rotation of the rotation body based on the detected rotating speed. The filter passes, as the encoder signal, only a signal having a frequency, outside a frequency band of a high-frequency signal of a high-frequency treatment instrument, of signals input to the rotating speed detector.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments, and together with the general description given above and the detailed description of the embodiments given below, serve to explain the principles.

FIG. 2 is a diagram illustrating an example of the filter characteristics of an LPF.

DETAILED DESCRIPTION

Figure 1:
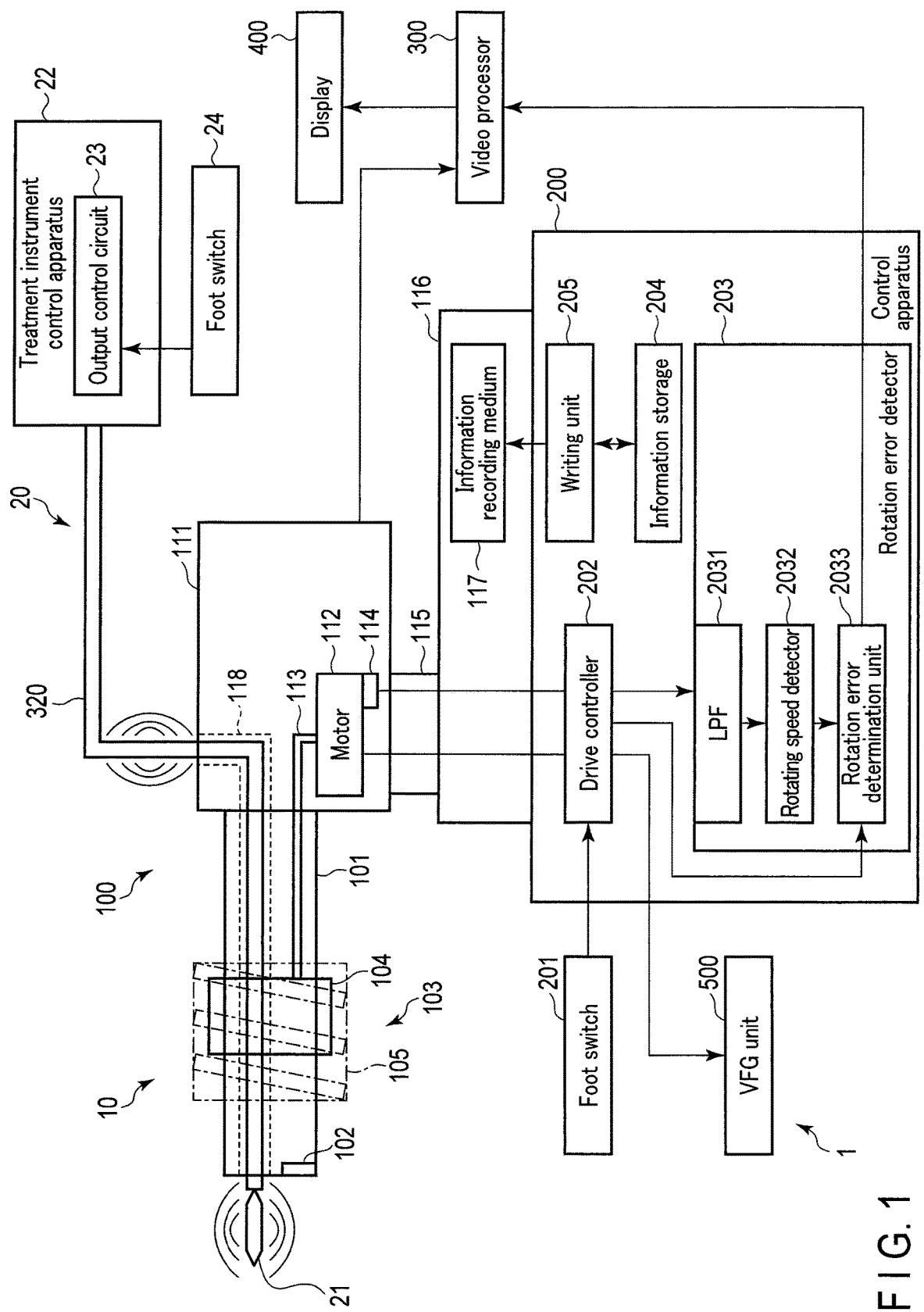
FIG. 1 is a diagram illustrating a configuration example of a surgical system according to an embodiment.

Hereinafter, embodiments will be described with reference to the drawings. FIG. 1 is a diagram illustrating a configuration example of a surgical system according to an embodiment. The surgical system 1 includes an endoscope apparatus 10 and a high-frequency treatment instrument 20.

The endoscope apparatus 10 includes an endoscope 100, a control apparatus 200, a video processor 300, a display 400, and a visual force gauge (VFG) unit 500. The endoscope 100 is configured to be connected to the control apparatus 200 via a connector 116 provided on the endoscope 100.

The endoscope 100 is a self-propelled endoscope apparatus including an insertion section 101 and an operation unit 111.

The insertion section 101 is a distal end portion of the endoscope 100. The insertion section 101 has an elongated shape and is configured to be flexible. Further, an imaging element 102 is provided at the distal end of the insertion section 101. The imaging element 102 images a subject existing on the distal end side of the insertion section 101 and acquires image data about the subject. Further, the insertion section 101 is provided with a self-propelled mechanism 103. The self-propelled mechanism 103 includes a rotation body 104 and a spiral tube 105. The rotation body 104 is provided on an outer peripheral surface of the insertion section 101 so as to be rotatable around a longitudinal axis. The spiral tube 105 is provided so as to have a spiral fin around the rotation body 104. The spiral tube 105 may be configured to be removable from the rotation body 104. The spiral tube 105 may also be configured to be disposable.

The operation unit 111 is a part that is gripped by the user, and includes various operation members for operating the endoscope 100. Further, the operation unit 111 includes a motor 112. The motor 112 generates a driving force for the self-propelled mechanism 103. When the motor 112 rotates, the rotational motion is transmitted to the rotation body 104 via a transmission member 113 extending from the inside of the operation unit 111 to the insertion section 101. As the rotation body 104 rotates, the spiral tube 105 rotates. Due to the rotation of the spiral tube 105, a propulsive force is generated in the insertion section 101. This propulsive force causes the insertion section 101 to self-propel. The self-propulsion of the insertion section 101 assists in the tasks of insertion and removal of the insertion section 101 by the user. Further, for example, a rotary encoder 114 is provided near the motor 112. The encoder 114 includes a scale and a sensor head. The scale is attached to, for example, the motor 112 and rotates along with the rotation of the motor 112. A predetermined periodic pattern (for example, an optical pattern) is formed on this scale. The sensor head outputs a two-phase encoder signal having a predetermined phase difference (for example, 90 degrees) corresponding to a pattern change caused by relative displacement from the scale.

A universal cable 115 is connected to the operation unit 111. The universal cable 115 is provided with various signal lines for transmitting and receiving signals between the endoscope 100 and the control apparatus 200. The universal cable 115 is connected to the connector 116. As described above, the endoscope 100 and the control apparatus 200 are connected via the connector 116. The connector 116 is provided with an information recording medium 117 comprising, for example, a ROM. In the information recording medium 117, individual information of the endoscope 100, drive information (a log of a current value supplied to the motor 112, information on presence/absence of a rotation error of the rotation body 104, etc.) related to the rotation body 104 during the operation of the rotation body 104, and the like are recorded.

Furthermore, the endoscope 100 includes an instrument channel 118 for inserting a treatment tool or the like from the operation unit 111 to the distal end of the insertion section 101. The instrument channel 118 is a hole through which a high-frequency treatment instrument 20 such as a high-frequency knife is passed to the distal end of the endoscope 100. A tip 21 of the high-frequency treatment instrument 20 or the like inserted into the instrument channel 118 from the operation unit 111 side is configured to protrude from the distal end of the insertion section 101. The user can perform treatment using the high-frequency treatment instrument 20 or the like protruding from the distal end of the insertion section 101.

The high-frequency treatment instrument 20 in the present embodiment is a high-frequency treatment instrument configured to generate a high-frequency signal for the high-frequency knife or the like. A treatment instrument control apparatus 22 is connected to the high-frequency treatment instrument 20. The treatment instrument control apparatus 22 controls a high frequency signal generated at the tip 21 of the high-frequency treatment instrument 20. The treatment instrument control apparatus 22 includes an output control circuit 23. The output control circuit 23 generates high-frequency power at the tip 21 in accordance with the amount of depression of the foot switch 24. From the viewpoint of safety, it is desirable that the high-frequency signal generation in the high-frequency treatment instrument 20 and the self-propulsion of the insertion section 101 should not be performed simultaneously. Accordingly, it is assumed that the user does not perform an operation for causing the insertion section 101 to self-propel while stepping on the foot switch 24. Of course, the control apparatus 200 may determine the usage state of the high-frequency treatment instrument 20, and control may be performed to limit the rotation of the motor 112 according to the determination result.

The control apparatus 200 includes a foot switch 201, a drive controller 202, a rotation error detector 203, an information storage 204, and a writing unit 205. The control apparatus 200 comprises a CPU, ASIC, FPGA, or the like.

The foot switch 201 includes a forward pedal and a backward pedal. When the forward pedal is stepped on by the user, the forward pedal generates an instruction signal for causing the motor 112 to rotate forward. The backward pedal generates an instruction signal for reversing the rotation of the motor 112 when stepped on by the user.

The drive controller 202 controls the rotation operation of the motor 112. The drive controller 202 supplies a current to the motor 112 so that the motor 112 rotates at a rotating speed corresponding to the amount of depression of the foot switch 201. For example, the drive controller 202 receives an encoder signal output from the encoder 114. The drive controller 202 controls the magnitude and direction of the current flowing through the motor 112, so that the actual rotating speed of the motor 112 detected from the encoder signal matches the rotating speed according to the amount of depression of the foot switch 201. Furthermore, the drive controller 202 outputs the encoder signal output from the encoder 114 to the rotation error detector 203.

The rotation error detector 203 receives the encoder signal output from the encoder 114 and detects an error in the rotation of the rotation body 104 based on the acquired encoder signal. The error in rotation of the rotation body 104 is, for example, a state in which the rotation body 104 is not rotating even though the foot switch 201 is stepped on, or conversely the rotation body 104 is rotating even though the foot switch 201 is not stepped on. The rotation error detector 203 includes a low pass filter (LPF) 2031, a rotating speed detector 2032, and a rotation error determination unit 2033. The LPF 2031, the rotating speed detector 2032, and the rotation error determination unit 2033 are configured by, for example, an FPGA. The LPF 2031, the rotating speed detector 2032, and the rotation error determination unit 2033 may be configured by an ASIC other than the FPGA.

The LPF 2031 is provided immediately before the rotating speed detector 2032 and passes, as encoder signals, only signals that have a frequency lower than the frequency of the high-frequency signal generated at the tip of the high-frequency treatment instrument 20 out of the signals input to the rotating speed detector 2032. FIG. 2 is a diagram illustrating an example of the filter characteristics of the LPF 2031. The horizontal axis in FIG. 2 represents the frequency, and the vertical axis in FIG. 2 represents the number of data samples that pass through the LPF 2031 when, for example, m samples of data of one period of the corresponding frequency are input to the LPF 2031. In this example, it is assumed that the edge of the encoder signal is detected when the number of samples of data passing through the LPF 2031 is n or more, while m samples of data are input. The detection of the edge of the encoder signal means that a change in the scale pattern has been detected. In this case, the cut-off frequency fc of the LPF 2031 in this embodiment is a frequency at which the number of data samples output from the LPF 2031 is less than n samples. In this embodiment, such a cut-off frequency fc is set to be lower than the frequency of the high-frequency signal used in the high-frequency treatment instrument 20 and higher than the frequency of the encoder signal. This is because the frequency of the high frequency signal used in the high-frequency treatment instrument 20 is usually sufficiently higher than the frequency of the encoder signal.

The rotating speed detector 2032 detects the current rotating speed of the motor 112 from the encoder signal that has passed through the LPF 2031. For example, the rotating speed detector 2032 detects the rotating speed by counting the number of edges of the encoder signal.

The rotation error determination unit 2033 determines a rotation error of the rotation body 104 from the control state of the motor 112 by the drive controller 202 and the rotating speed detected by the rotating speed detector 2032. For example, the rotation error determination unit 2033 determines that there is an error in the rotation of the rotation body 104 when the motor 112 is not rotating even though a current is supplied from the drive controller 202 to the motor 112. The fact that the motor 112 is not rotating means that the rotating speed of the motor 112 is zero, for example. In such a case, the rotation error determination unit 2033 notifies the user that there is an error in the rotation of the rotation body 104 through the display 400 or the VFG unit 500. Further, for example, the rotation error determination unit 2033 determines that there is an error in the rotation of the rotation body 104 when the motor 112 is rotating even though no current is flowing from the drive controller 202 to the motor 112. The fact that the motor 112 is rotating means that the rotating speed of the motor 112 is not zero. Also in such a case, the rotation error determination unit 2033 notifies the user that there is an error in the rotation of the rotation body 104 through the display 400 or the VFG unit 500.

The information storage 204 comprises a RAM, for example, and temporarily stores drive information generated by the drive controller 202, for example. The drive information stored in the information storage 204 is recorded in the information recording medium 117 of the endoscope 100 at a predetermined writing timing.

The writing unit 205 determines the timing for writing the drive information stored in the information storage 204 into the information recording medium 117. The writing unit 205 writes the drive information stored in the information storage 204 into the information recording medium 117 when determining that it is time to write the drive information into the information recording medium 117. The writing unit 205 normally writes drive information into the information recording medium 117 at predetermined intervals. However, the writing unit 205 does not write drive information when it is considered that a high-frequency signal is generated in the high-frequency treatment instrument 20. As described above, if the generation of the high frequency signal in the high-frequency treatment instrument 20 and the self-propulsion of the insertion section 101 are not performed simultaneously, the high-frequency signal cannot be generated in the high-frequency treatment instrument 20 while the foot switch 201 is being depressed. Therefore, the writing unit 205 determines that it is the timing to write drive information while the foot switch 201 is being stepped on. By not writing the drive information at the timing when the high-frequency treatment instrument 20 is considered to be generating a high-frequency signal, it is possible to prevent an occurrence of a writing error due to mixing of a noise by a high-frequency signal generated in the high-frequency treatment instrument 20 into the drive information.

The video processor 300 processes image data obtained by imaging with the imaging element 102 of the endoscope 100 to generate display image data. In addition, the video processor 300 displays an image obtained by the endoscope 100 on the display 400 based on the display image data.

The display 400 which is, for example, a liquid crystal display, displays various types of images. The images include a display image obtained via the endoscope 100 and a display image for notifying an error in the rotation of the rotation body 104. In the notification of the error in the rotation body 104, in response to an instruction from the rotation error determination unit 2033, the video processor 300 includes a display image for notifying an error in the rotation in a picture-in-picture (PIP) format in the display image obtained via the endoscope 100.

The VFG unit 500 includes, for example, a plurality of LED indicators, and displays the magnitude of the current, which the drive controller 202 causes to flow to the motor 112, by the number of LED indicators that are turned on. The magnitude of the current flowing through the motor 112 corresponds to the magnitude of the torque of the motor 112. Furthermore, the VFG unit 500 turns on the LED indicator in a pattern different from the normal display when notifying the error in the rotation of the rotation body 104.

Figure 3:
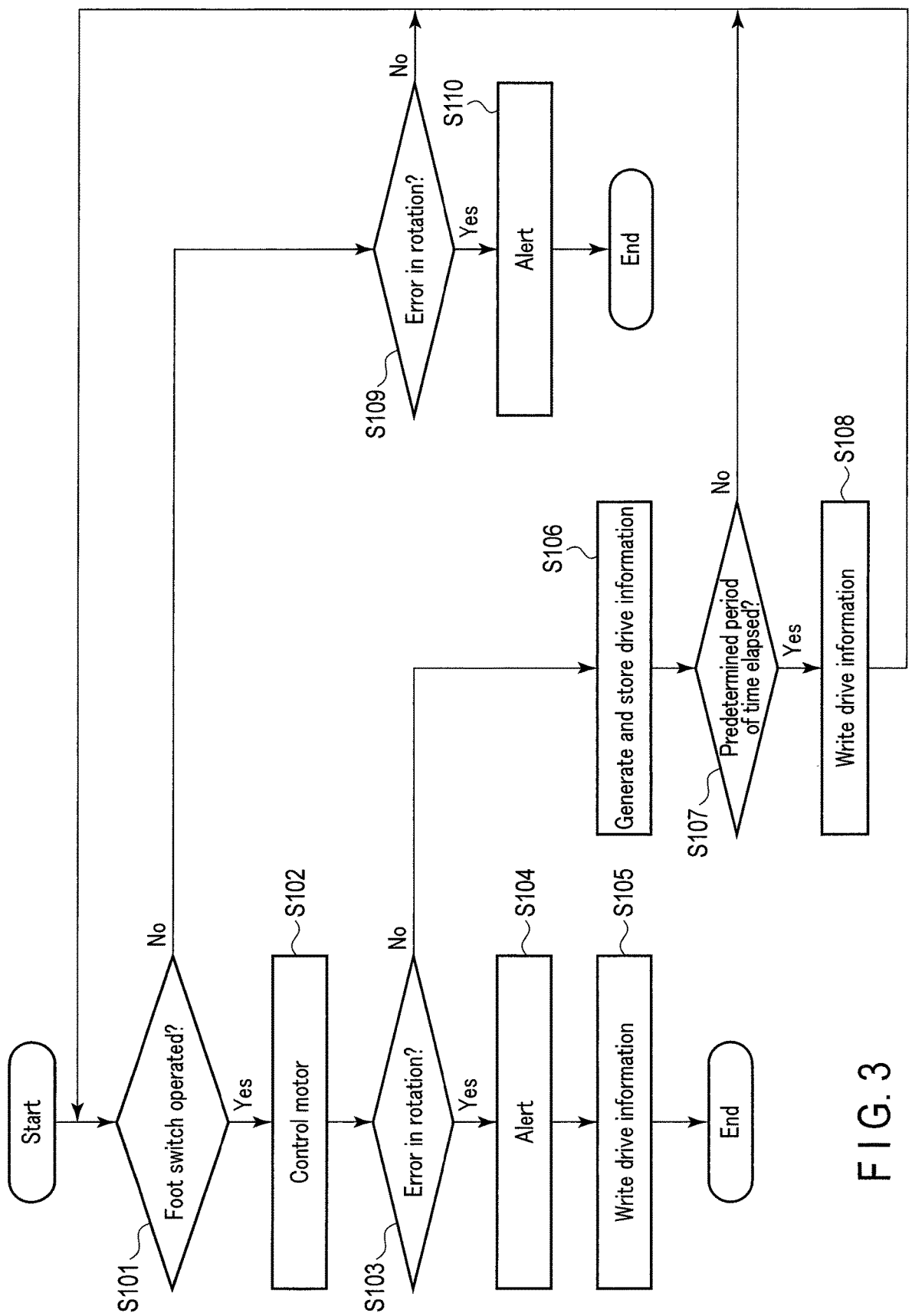
FIG. 3 is a flowchart for explaining the operation of the surgical system.

Hereinafter, the operation of the surgical system 1 will be described. FIG. 3 is a flowchart for explaining the operation of the surgical system 1. The operation illustrated in FIG. 3 is controlled by the control apparatus 200. In parallel with the operation illustrated in FIG. 3, processing for displaying a display image based on the image obtained by the imaging element 102 on the display 400 is performed. Furthermore, when the power of the surgical system 1 is turned off, the processing ends regardless of the state of the processing at that time.

In step S101, the drive controller 202 determines whether or not the foot switch 201 is operated. If it is determined in step S101 that the foot switch 201 is operated, the processing proceeds to step S102. If it is determined in step S101 that the foot switch 201 is not operated, the processing proceeds to step S109.

In step S102, the drive controller 202 controls the current that flows through the motor 112 so that the rotating speed of the motor 112 becomes the rotating speed corresponding to the amount of depression of the foot switch 201. Thereafter, the processing proceeds to step S103.

In step S103, the rotation error determination unit 2033 determines whether or not there is an error in the rotation of the rotation body 104 from the control state of the motor 112 by the drive controller 202 and the rotating speed detected by the rotating speed detector 2032. For example, the rotation error determination unit 2033 determines that there is an error in the rotation of the rotation body 104 when the rotating speed of the motor 112 is zero. In step S103, since the foot switch 201 has been stepped on, the motor 112 rotates at a rotating speed corresponding to the amount of depression of the foot switch 201. However, when the motor 112 is not rotating for some reason, it is determined that there is an error in the rotation of the rotation body 104. If it is determined in step S103 that there is an error in rotation of the rotation body 104, the processing proceeds to step S104. If it is determined in step S103 that there is no error in rotation of the rotation body 104, the processing proceeds to step S106.

In step S104, the rotation error determination unit 2033 notifies the user that there is an error in the rotation of the rotation body 104 through the display 400 or the VFG unit 500. At this time, it is possible to also alert or report what kind of error has occurred.

In step S105, the writing unit 205 writes the drive information indicating that there is an error in the rotation of the rotation body 104 into the information recording medium 117 of the endoscope 100. Thereafter, the processing illustrated in FIG. 3 ends. Note that the writing unit 205 may be configured to determine whether or not the drive information has been normally written. In this case, if the writing is not normally performed, the writing can be performed again at the next writing timing.

In step S106, the writing unit 205 stores, in the information storage 204 as drive information, the value of the current and the like that the drive controller 202 causes to flow to the motor 112.

In step S107, the writing unit 205 determines whether or not a predetermined period of time (for example, 15 seconds) has elapsed. If it is determined in step S107 that the predetermined period of time has elapsed, the processing proceeds to step S108. If it is determined in step S107 that the predetermined period of time has not elapsed, the processing returns to step S101.

In step S108, the writing unit 205 writes the drive information stored in the information storage 204 into the information recording medium 117 of the endoscope 100. Thereafter, the processing returns to step S101. Note that the writing unit 205 may be configured to determine whether or not the drive information has been normally written. In this case, if the writing is not normally performed, the writing can be performed again at the next writing timing.

In step S109, the rotation error determination unit 2033 determines whether or not there is an error in the rotation of the rotation body 104 from the control state of the motor 112 by the drive controller 202 and the rotating speed detected by the rotating speed detector 2032. For example, the rotation error determination unit 2033 determines that there is an error in the rotation of the rotation body 104 when the rotating speed of the motor 112 is not zero. In step S109, since the foot switch 201 has not been stepped on, the motor 112 normally does not rotate. However, the motor 112 may rotate due to the influence of an external force from the body, a short circuit failure of the motor 112, or the like. In such a case, it is determined that there is an error in the rotation of the rotation body 104. If it is determined in step S109 that there is an error in the rotation of the rotation body 104, the processing proceeds to step S110. If it is determined in step S109 that there is no error in the rotation of the rotation body 104, the processing proceeds to step S101.

In step S110, the rotation error determination unit 2033 notifies the user that there is an error in the rotation of the rotation body 104 through the display 400 or the VFG unit 500. Thereafter, the processing illustrated in FIG. 3 ends. At this time, it is possible to also alert or report what kind of error has occurred. Note that, at the timing of step S110, since the foot switch 201 has not been stepped on, drive information is not written. On the other hand, the drive information may be stored.

As described above, according to the present embodiment, the LPF 2031 is arranged before the rotating speed detector 2032 for determining an error in the rotation in the rotation error determination unit 2033, and the signal that has passed through the LPF 2031 is used as the encoder signal. As described above, the high-frequency treatment instrument 20 may be used when the foot switch 201 has not been stepped on. In this case, there is a possibility that noise due to the high-frequency signal generated in the high-frequency treatment instrument 20 is superimposed on the encoder signal. Even if a high-frequency signal is generated in the high-frequency treatment instrument 20, the component of the high-frequency signal can be removed from the signal input to the rotating speed detector 2032 by the LPF 2031 having a lower cutoff frequency than the high-frequency signal generated in the high-frequency treatment instrument 20. As a result, for example, the rotating speed detector 2032 is prevented from erroneously counting the rotating speed due to noise caused by a high-frequency signal, though the motor 112 has stopped normally while the foot switch 201 is not being stepped on. Thus, in this embodiment, even though a high-frequency treatment instrument is used, it is possible to correctly determine whether there is an error in the rotation of the rotation body 104.

Further, since the LPF 2031 is disposed immediately before the rotating speed detector 2032, regardless of where in the path from the motor 112 to the rotating speed detector 2032 noise due to the high frequency signal is mixed, the signal input to the rotating speed detector 2032 is a signal from which the high frequency signal component has been removed.

The present invention has been explained based on the embodiment; however, the present invention is not limited to the embodiment. The present invention may, of course, be modified in various ways without departing from the spirit and scope of the invention. For example, in the above-described embodiment, the LPF is used, since it is assumed that the frequency of the encoder signal is lower than the frequency of the signal generated in the high-frequency treatment instrument 20. On the other hand, when the frequency of the encoder signal is higher than the frequency of the signal generated in the high-frequency treatment instrument 20, a high pass filter (HPF) having a cutoff frequency higher than the frequency of the signal generated in the high-frequency treatment instrument 20 is used. That is, the filter disposed immediately before the rotating speed detector 2032 may be any filter that allows passage of signals having frequencies outside the frequency band of the signal generated in the high-frequency treatment instrument 20.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An apparatus, comprising:
a rotation body provided on an outer peripheral surface of an elongated insertion section and configured to be rotatable around a longitudinal axis;
a motor configured to rotate the rotation body;
a drive controller configured to control driving of the motor;
a rotating speed detector configured to detect a rotating speed of the motor based on an encoder signal output from an encoder;
a rotation error determination circuit configured to determine an error in rotation of the rotation body based on the detected rotating speed; and
a filter configured to pass, as the encoder signal, only a signal having a frequency, outside a frequency band of a high-frequency signal of a high-frequency treatment instrument, of signals input to the rotating speed detector.

2. The apparatus according to claim 1, wherein the filter is provided immediately before the rotating speed detector.

3. The apparatus according to claim 2, wherein the rotation error determination circuit determines that there is an error in rotation of the rotation body when detecting that the motor is rotating based on the detected rotating speed even though the drive controller is controlling to stop the motor.

4. The apparatus according to claim 2, wherein the encoder is provided near the motor.

5. The apparatus according to claim 2, wherein the rotation error determination circuit compares the detected rotating speed with a rotating speed of the motor based on a current input by the drive controller to the motor, to determine whether or not there is an error in the rotation of the rotation body.

6. The apparatus according to claim 2, wherein the frequency band of the high-frequency signal of the high-frequency treatment instrument is higher than the frequency of the encoder signal, and
   wherein the filter is a low-pass filter having a cutoff frequency lower than the frequency band of the high-frequency signal of the high-frequency treatment instrument and higher than the frequency of the encoder signal.

7. The apparatus according to claim 2, further comprising:
   a foot switch configured to operate the motor; and
   an information recording medium configured to record information on a driving state of the motor;
   wherein the drive controller records information on the driving state in the information recording medium when the foot switch is operated.

8. A control apparatus of an apparatus including a rotation body provided on an outer peripheral surface of an elongated insertion section and configured to be rotatable around a longitudinal axis; a motor configured to rotate the rotation body, the control apparatus comprising:
   a drive controller configured to control driving of the motor;
   a rotating speed detector configured to detect a rotating speed of the motor based on an encoder signal output from an encoder;
   a rotation error determination circuit configured to determine an error in rotation of the rotation body based on the detected rotating speed; and
   a filter configured to pass, as the encoder signal, only a signal having a frequency, outside a frequency band of a high-frequency signal of a high-frequency treatment instrument, of signals input to the rotating speed detector.

9. The control apparatus according to claim 8, wherein the filter is provided immediately before the rotating speed detector.

10. The control apparatus according to claim 9, wherein the rotation error determination circuit determines that there is an error in rotation of the rotation body when detecting that the motor is rotating based on the detected rotating speed though the drive controller is controlling to stop the motor.

11. The control apparatus according to claim 9, wherein the encoder is provided near the motor.

12. The control apparatus according to claim 9, wherein the rotation error determination circuit compares the detected rotating speed with a rotating speed of the motor based on a current input to the motor by the drive controller, to determine whether or not there is an error in the rotation of the rotation body.

13. The control apparatus according to claim 9, wherein the frequency band of the high-frequency signal of the high-frequency treatment instrument is higher than the frequency of the encoder signal, and
   wherein the filter is a low-pass filter having a cutoff frequency lower than a frequency band of a high-frequency signal of the high-frequency treatment instrument and higher than a frequency of the encoder signal.

14. A control method comprising:
   in response to an operation of a foot switch, rotating a rotation body provided on an outer peripheral surface of an elongated insertion section by a motor and configured to be rotatable around a longitudinal axis;
   detecting a rotating speed of the motor based on an encoder signal output from an encoder;
   determining an error in rotation of the rotation body based on the detected rotating speed; and
   when there is an error in the rotation, after warning, recording information on a driving state of the motor in an information recording medium; and
   when there is no error in the rotation, after a lapse of a predetermined period of time, recording the information on the driving state of the motor in the information recording medium.

* * * * *